United States Patent [19]

Fivez

[11] Patent Number: 5,533,088
[45] Date of Patent: Jul. 2, 1996

[54] METHOD OF COMPENSATING FOR RADIATION SCATTER IN AN X-RAY IMAGING SYSTEM

[75] Inventor: Christiaan Fivez, Heverlee, Belgium

[73] Assignee: AGFA-Gevaert, Mortsel, Belgium

[21] Appl. No.: 465,838

[22] Filed: Jun. 6, 1995

[30] Foreign Application Priority Data

Jun. 23, 1994 [EP] European Pat. Off. ............ 94201801

[51] Int. Cl.⁶ .................................................. H05G 1/64
[52] U.S. Cl. ............................... 378/98.4; 378/98.2
[58] Field of Search .......................................... 378/98.4

[56] References Cited

U.S. PATENT DOCUMENTS

4,549,307  10/1985  Macovski ............................... 378/98.4
4,688,242   8/1987  Ema ....................................... 378/98.4
4,823,370   4/1989  Kikuchi ................................. 378/98.4

*Primary Examiner*—Craig E. Church
*Attorney, Agent, or Firm*—Richard J. Birch

[57] ABSTRACT

A shield comprising bodies that are opaque to x-rays, is positioned during a known fraction f of an exposure time T between an object to be imaged and a radiation source in a two-dimensional x-ray imaging system. The radiation scatter is calculated from the following values: the radiation received by a radiation detector at the temporarily shielded areas, the radiation received by the detector in areas closely adjacent to said temporarily shielded areas and the fraction f. Scatter values are subtracted from values representing radiation transmitted by the object to obtain a scatter compensated image of the object.

6 Claims, 7 Drawing Sheets

METHOD OF COMPENSATING FOR RADIATION SCATTER IN AN X-RAY IMAGING SYSTEM

BACKGROUND OF THE INVENTION

1. Field of the Invention

The present invention relates to a method for compensating x-ray imaging systems for radiation scatter.

2. Description of the Prior Art

In x-ray imaging systems, the total flux of detected radiation consists not only of photons that did not interact with the elements of the attenuating object being imaged but also of radiation scatter. Specifically for systems using area detectors the amount of radiation scatter can be very large. For a large class of applications, such as energy-selective imaging, this radiation can be an important source of error and must be compensated in order to have satisfying results.

A lot of work has been done already in searching good methods for compensating x-ray imaging systems for radiation scatter.

The use of grids or air gaps reduces but doesn't eliminate the radiation scatter. For many applications, as for dual-energy subtraction imaging, it is not sufficient.

Several analytical models, representing the scatter—some of them use point spread functions—are proposed in the prior art. They require parameters the values of which are difficult to obtain and in most cases to be found experimentally. These models do not give satisfying results in some practical applications.

In the prior art, some investigators (Molloi SY, Mistretta Calif. Scatter-glare correction in quantitative dual-energy fluoroscopy. Med. Phys. 1988; 15:289–297) use correction tables for a specific application that give a hypothesized relationship between the detected grey level in a certain pixel and the scatter fraction. For most applications they are rough estimations with insufficient accuracy.

In U.S. Pat. No. 4,549,307 a method is used in which two x-ray irradiations of an object are made: one with a disk sampler, consisting of an array of small lead beam stops above the object, and one without the sampler. In the shadow of each disk only scattered radiation is detected and the average of the pixels values in this shadow gives the value of the radiation scatter at that location. By interpolation of the sample values of the radiation scatter distributed over the image area, an estimation of the radiation scatter values in the whole image is generated. The scatter corrected image is obtained by subtracting the scatter-surface from the second image, where no beam stop array was positioned. One disadvantage of this method is that one needs two separate images, and thus two separate shots, of the object. In medical applications, this means that the patient (=the object) receives a larger x-ray dose and that he may have moved between the two shot's. Switching quickly detectors and disk samplers asks for a mechanically complicated system. Another implementation of the method with the lead beam stops in which only the x-ray irradiation with the disk sampler is made has the disadvantage that all the information about the object is lost under the beam stops. This can be an important disadvantage.

In the prior art, another method for scatter radiation compensation (Shaw C. A novel technique for simultaneous acquisition of primary and scatter image signals. SPIE Vol. 1651 Medical Imaging VI: Instrumentation (1992), p. 222–233), is the so-called primary-modulation-demodulation technique. The primary x-ray distribution is modulated and demodulated with two filters of equal material and thickness placed on the tube and detector sides of the objects. The modulation-demodulation process results in a reduction of scatter signals in selected regions of the image. It leaves the overall primary distribution signal unchanged. The signal drop of the radiation scatter can be measured and used to estimate the scatter radiation signal in the selected regions. Although the PMD method allows both primary and scatter signals to be acquired simultaneously, it has two main disadvantages: it is unknown how the drop in scatter radiation relates to location, scattering geometry, object (mostly a patient), etc.. Another disadvantage is that it is practically impossible to match the modulator and the demodulators. Therefore the results are based on rough estimates and the accuracy is reduced.

A recently developed technique is described by C. Fivez in unpublished European application no. 93.203671. The methods according to that invention are based on one irradiating shot of the object. After scatter radiation compensation, the information about the object is not lost in any location of the object image. By comparing the detected signal under a partially transparent body (e.g. disk or strip), positioned between the x-ray source and the object being imaged, with the signal in the image near the border of the shadow of the partially transparent body, the radiation scatter signal in the location of the shadow of the body is calculated. In case of a polychromatic source, calibration with two known materials allows accurate calculation of the radiation scatter. The partially transparent bodies are positioned at several locations between object and source and, by means of an interpolation technique, the radiation scatter in every location of interest can be calculated. The radiation scatter image is subtracted from the original image of the object. The primary signal (=without radiation scatter) in the location of the bodies has undergone an extra drop because of the partially transparent body but the information about the object under the body is not lost. The method allows, with only one shot of the object, to compensate for radiation scatter without loosing information about the object. For accurate calculation of the scattered radiation one needs a calibration as mentioned before. In energy-selective imaging, one often uses such calibration, so that in such cases it is not a problem. Nevertheless, in other application areas, the calibration can be an objection, for it complicates the procedure. Another disadvantage of the method is that the materials in the object and of the partially transparent bodies must belong to (a large) group of materials. It can not be whatever materials. For the partially transparent bodies a consequence can be that the height of the bodies must be relatively large, if one wants a reasonable accuracy. Such heights can cause some geometric artefacts.

U.S. Pat. No. 4,688,242 discloses a X-ray imaging system wherein X-ray image data are calculated from scattered X-ray intensity distribution data and transmission X-ray data.

The transmission X-ray image data are obtained by irradiating an object with X-rays and detecting the transmitted rays by means of an X-ray image detection means such as an image intensifier and a camera.

The scattered X-ray intensity distribution data are calculated on the basis of (i) a plurality of transmission X-ray data obtained by irradiating an object with X-rays with a mask member, comprising a plurality of X-ray shielding regions distributed in a predetermined pattern being located at different positions in said X-ray radiation field and (ii) on transmission X-ray data obtained by irradiating said object with X-rays when said mask member is located outside said X-ray radiation field.

The method applied in this X-ray imaging system comprises (1) the insertion of the mask member between the X-ray image detection means and the X-ray source and (2) the shifting of the mask member between (two) predetermined positions in the X-ray irradiation field. In particular the movement of the mask means from a position outside the X-ray radiation field to a position in between the X-ray source and the object is time consuming and inadequate for application in chest imaging since the position of the patient could have changed within the period of time required to perform the displacement of the shield. The method is further not adapted for application in a method wherein an area detector such as a photostimulable phosphor screen is used.

In the article by F. Wagner, A. Macovski and D. Nishimura entitled 'Dual Energy X-ray projection imaging: Two sampling schemes for the correction of scattered radiation', published in Medical Physics, Vol. 15, Oct. 1988, p. 732–748 two methods have been disclosed for the correction of scatter.

Each method requires two measurements and each method involves placing an opaque sampling grid between the source and the object.

In the first method, the grid is an array of lead disks present during one measurement. Using this grid, an estimate of the scatter field is generated and subtracted from the second measurement yielding a scatter-corrected image. This method also comprises the time-consuming step of positioning the grid in between source and object, so it is also inadequate for most chest applications.

In the second described method the grid is present during both measurements and is shifted by one-half of a strip spacing to completely sample the image.

An image to be corrected is generated, an estimate of the scatter field and a scatter corrected image are generated. This method is disadvantageous because at locations beneath a lead disk the original signal is lost.

SUMMARY OF THE INVENTION

Objects of the Invention

It is an object of the present invention to provide a method of compensating for scattered radiation in a two-dimensional x-ray imaging system.

It is a further object of the present invention to overcome the disadvantages of the prior art methods.

Statement of the Invention

The objects of the invention are achieved by a method of compensating for scattered radiation in a 2-dimensional x-ray system comprising the steps of:

exposing an object an a radiation shield comprising a plurality of X-ray opaque bodies, to x-rays emitted by an x-ray source during an exposure time T, the shield being positioned between said x-ray source and said object, so that during a known fraction $f_j$ ($f_j>0$ and $f_j<1$) of said exposure time T a plurality of areas j of said object are temporarily shielded by said opaque bodies, exposing a two-dimensional radiation detector to x-rays transmitted by a combination of said object and said shield during said exposure time T, measuring radiation $E_1$ received by said detector at temporarily shielded areas j of said radiation detector, measuring radiation $E_2$ received by said detector in areas closely adjacent to said temporarily shielded areas j that have not been shielded by said opaque bodies during said exposure time T, calculating radiation scatter values $E_s$ received by said detector at said temporarily shielded areas j of said radiation detector, by using said fraction $f_j$ of said exposure time T and said measured radiation $E_1$ and said measured radiation $E_2$, calculating radiation scatter values for all areas of said detector means by interpolating the calculated radiation scatter values $E_s$, measuring radiation received by said radiation detector at all areas of said radiation detector where it has not yet been measured, and subtracting interpolated radiation scatter values from the measured radiation values for all areas of said radiation detector.

It is an advantage of the invention to be able to calculate the scatter radiation component in the image with a high degree of accuracy by means of an exposure that leads to only one image of the object being imaged. It is a further advantage to be able to compensate the image of the object for this radiation scatter, without losing the information about the primary radiation distribution in any location of the object.

BRIEF DESCRIPTION OF THE DRAWINGS

Specific embodiments of the invention will be described below with reference to the drawings wherein.

DESCRIPTION OF THE PREFERRED EMBODIMENTS

Figure 1:
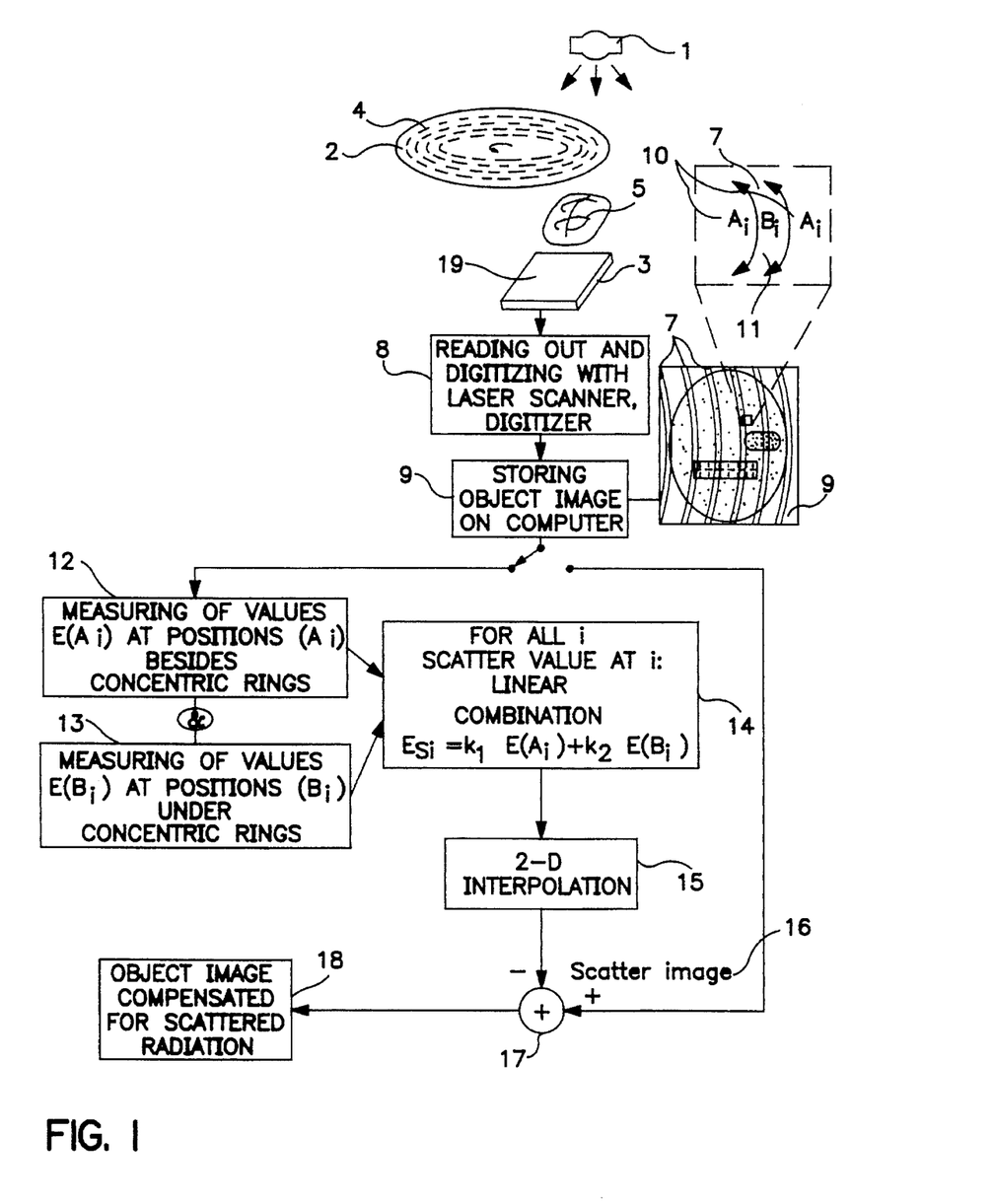
FIG. 1 is a functional block diagram illustrating one embodiment of the method for radiation scatter compensation according to the invention.

FIG. 1 is a schematic diagram of one embodiment of the method for radiation scatter compensation according to the invention. The method will be realized on an x-ray imaging system, such as the computed radiographic system of FIG. 1. This system is just an example. Other x-ray imaging systems are possible. X-Radiation from a source 1 is directed through an object 5 to an area detector such as a photostimulable phosphor screen 3 positioned in a visible light opaque cassette 19, whereby the x-ray image is latently stored on the phosphor screen 3. Suitable photostimulable phosphors are well known in the art; an example is e.g. described in European patent application 503 702 published Sep. 16, 1992. The latent image of phosphor screen 3 is then read out and digitized 8 by a laser scanner digitizer and converted into a grey value digitized image 9 which is stored on a computer and can be displayed. Radiation received by phosphor sheet 3 includes primary radiation but also a significant amount of scattered radiation which can cause a significant error in the displayed image. In accordance with the invention a calculation of the radiation scatter is performed and the image is then compensated by subtraction of the scattered radiation. After subtraction of the scattered radiation information about the primary radiation distribution is not lost in any location of the image. The calculation of the radiation scatter according to the invention is in the embodiment of FIG. 1 made possible by positioning a circular shield 2 between source 1 and object 5. The shield 2 comprises a number of opaque strips 4, positioned on concentric rings 7 around the centre of shield 2. The strips 4 have a constant width which is the same as that of the concentric rings 7, whereby the strips are curved exactly the same as the concentric circles. The shield 2 is made in such a way that for the concentric rings 7 a constant fraction f of the area of every concentric rings 7 is covered by opaque strips 4. The fraction f does not have to be the same for every concentric, but it is simpler. Anyway, the fraction f corresponding with each concentric ring is to be known. In the following it is assumed that every specific concentric ring has its own specific value of f. In the embodiment of FIG. 1 the strips 4 are separated from each other along the concentric rings 7 by equal distances. The shield 2 is turning around its axis with a high constant angular speed ω during the exposure time T. During the fraction f, corresponding with a specific concentric ring, of the exposure time T the area of the concentric ring is shielded by the strips 4. The strips shield the primary radiation. Let us consider a set of locations i along the concentric rings. We measure 13 the total detected intensity E(Bi) at position 11 Bi on a concentric ring 7 and we measure 12 the total detected intensities E(Ai) at positions 10 Ai next to position 11 Bi and next to the concentric ring 7. Since we assume basically that the radiation scatter has a low spatial frequency, we assume also that the amount of radiation scatter in position Bi and in positions Ai is the same. The mean primary radiation intensity nevertheless differs in position Bi and in positions Ai since Bi was shielded during fraction f of T. A fraction of the difference of the mean primary intensity signal in Bi and in Ai can be caused by the variations of tissues in the object in the surrounding of Bi and Ai. If these variations are not too large, we can interpolate the mean values of the primary intensities in the positions Ai at both sides of the concentric ring. At this stage we don't know yet the primary radiation distribution around the location i. The scattered radiation signal $E_{si}$ in the local surrounding of location i is more or less constant; thus interpolating the total signal instead of only the primary radiation signal will not affect the scattered radiation signal. Then further on, by E(Ai) is meant the mentioned interpolated value at position Bi. In this way the difference between the primary intensity signal in Bi and in Ai is only caused by the shielding Bi during fraction f of T. The radiation scatter intensity signal in position Bi is then given by 14:

$$E_{si}=k1.E(Ai)+k2.E(Bi)$$

whereby $k1=(-(1-f)/f)$ and $k2=(1/f)$, and whereby f can be different for different concentric rings.

After having calculated 14 the radiation scatter $E_{si}$ for all locations i on the concentric rings we interpolate 15 these radiation scatter values for the whole image area and we obtain the scatter image 16. The scatter image 16 is subtracted from the original image 9 to obtain the object image 18 compensated for scattered radiation. In image 18 the concentric rings are contrasting with the area next to them because the primary radiation intensity signal on the rings 7 is a fraction f smaller then the primary radiation intensity signal just next to the rings. If wanted the image 18 can be compensated for the effect of the shielding on the rings by multiplying the primary intensity signal on a concentric ring 7 with factor (1/f). We can even more or less take into account the local profile of the radiation scatter in the area of the concentric rings. Since under the opaque shields itself no first order radiation scatter (—this means radiation which scatters for the first time in the volume an opaque shield—) is generated, a small deviation from a constant radiation scatter value can appear. The error made by assuming that the radiation scatter is constant is a small error. Nevertheless, one can estimate the shape of the mentioned profile to be more accurate.

In the embodiment of FIG. 1 the exposure time T may be short. If human patients are involved it may be of the same order as for a conventional radiograph.

The measuring of the signals in the described embodiment may be concurrent and does not have to be performed in a certain order.

Figure 2:
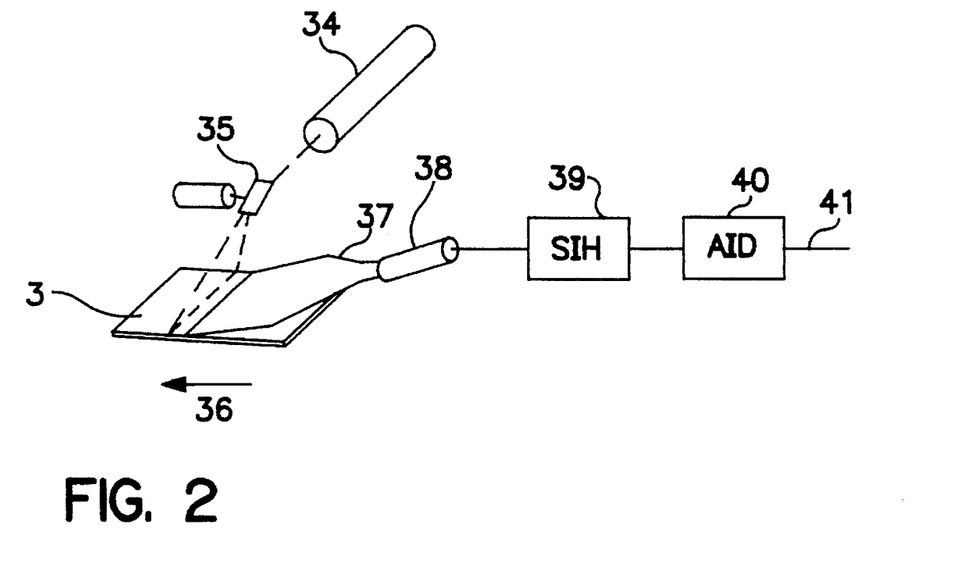
FIG. 2 is an example of a laser scanner digitizer.

FIG. 2 is an example of a laser scanner digitizer, such as is used in the embodiment of FIG. 1. The stored image (9 in FIG. 1) is read-out by scanning the phosphor screen 3 with stimulating rays emitted by laser 34. The stimulating rays are deflected into the main scanning direction by means of galvanometric deflection 35. Sub-scanning is performed by transporting the phosphor screen in the sub-scanning direction 36. The stimulated emission directed by means of a light collector 37 onto a photomultiplier 38 for conversion into an electric image representation. Next, the signal is sampled by a sample and hold circuit 39, and converted into a 12 bit signal by means of an analog to digital convertor 40. The digital signal can then be further applied to a signal processor (not shown) and/or to a monitor or a recorder for controlling the optical density of a soft- or hard copy image.

Figure 3:
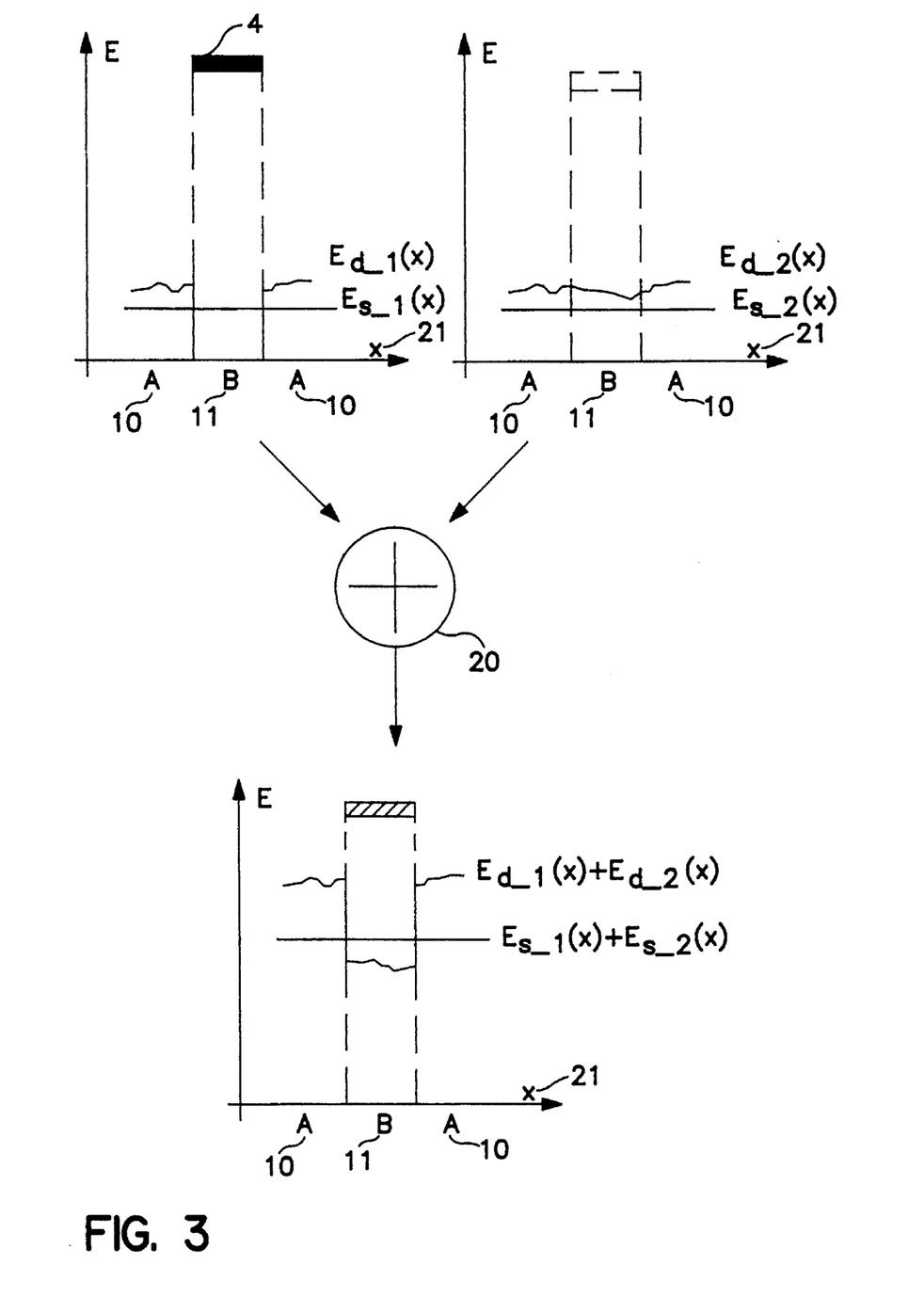
FIG. 3 is a schematic overview of the signals received by the detector under and next to a temporally shielded area.

Referring now to FIG. 3, this figure gives a schematic representation of the signals received under and next to the temporally shielded areas of FIG. 1. We represent the received total intensity signals by the symbol E, primary radiation signals by symbol $E_d$ and scattered radiation signals by symbol $E_s$. x represents the coordinate perpendicular to the opaque strips. In FIG. 3 three graphs are shown. The situation at the lower graph is the sum 20 of two components shown on top of the page. It illustrates the intensity signals received by the detector after the exposure time T is finished. The upper left picture illustrates the intensity signals received by the detector during the fraction f, corresponding with a specific concentric ring 7 of FIG. 1, of the exposure time T in which the area of the concentric ring 7 was shielded by opaque shields. Under the shields, in position 11 B, no primary radiation is received, only radiation scatter $E_{s1}(x)$. Next to the shielded area, in positions 10 A, radiation scatter $E_{s1}(x)$ and primary radiation $E_{d1}(x)$ is received. The upper right picture illustrates the intensity signals received by the detector during the fraction 1-f of the exposure time T in which the same areas under the concentric ring as from the upper left picture were not shielded. The scattered radiation signal is the small area around positions B and A is assumed to be constant. The radiation scatter $E_{s2}(x)$ is a fraction $((1-f)/f)$ of $E_{s1}(x)$. Now imaging for a moment that there are no variations in the object at the location of B and A. Then the primary radiation signal $E_{d-2}(x)$ in the positions A is a fraction $((1-f)/f)$ of the primary radiation signal $E_{d1}(x)$ in the same positions. But in position B, no primary radiation reached the detector during fraction f of T. But mostly there are local variations in the object, then, for the primary radiation signals $E_{d1}(x)$ and $E_{d2}(x)$ is the same reasoning valid as in the comment for FIG. 1. It was said there that local variations in the object may cause that the difference in primary radiation between position B and positions A is not only caused by the effect of presence of the opaque shield 4. For the reason we can take an interpolated value for the signals in positions A. We interpolate the total radiation signals of positions A. This interpolation does not affect the scattered radiation signal since it is constant. On the other hand the interpolation gives us a better estimate of the mean primary radiation signals.

So, if we take for the primary radiation signals $E_{d1}$ and $E_{d2}$ mean values or interpolated values as described before, we measure in positions A in B total radiation signals:

$$\text{In A: } E(A)=E_{d1}+E_{d2}+E_{s1}+E_{s2} \qquad (1)$$

$$\text{In B: } E(B)=E_{d2}+E_{s1}+E_{s2} \qquad (2)$$

The total amount of scattered radiation in position B is $E_s$:

$$E_s=E_{s1}+E_{s2} \qquad (3)$$

We showed that:

$$E_{d2}=((1-f)/f).E_{d1} \qquad (4)$$

So for equations (1) and (2) we get:

$$E(A)=(1/f).E_{d1}+E_s \qquad (5)$$

$$E(B)=((1-f).E_{d1}+E_s \qquad (6)$$

So finally we get for the scattered radiation signal in positions B and A:

$$E_s=E(B)/f-((1-f)/f).E(A) \qquad (7)$$

It is already mentioned above that we could also take into account the locale profile of the radiation scatter in the area of the concentric rings. Since under the opaque shields it self no first order radiation scatter is generated, a small deviation from a constant radiation scatter value can appear. One could estimate the shape of the mentioned profile to be more accurate.

Figure 4:
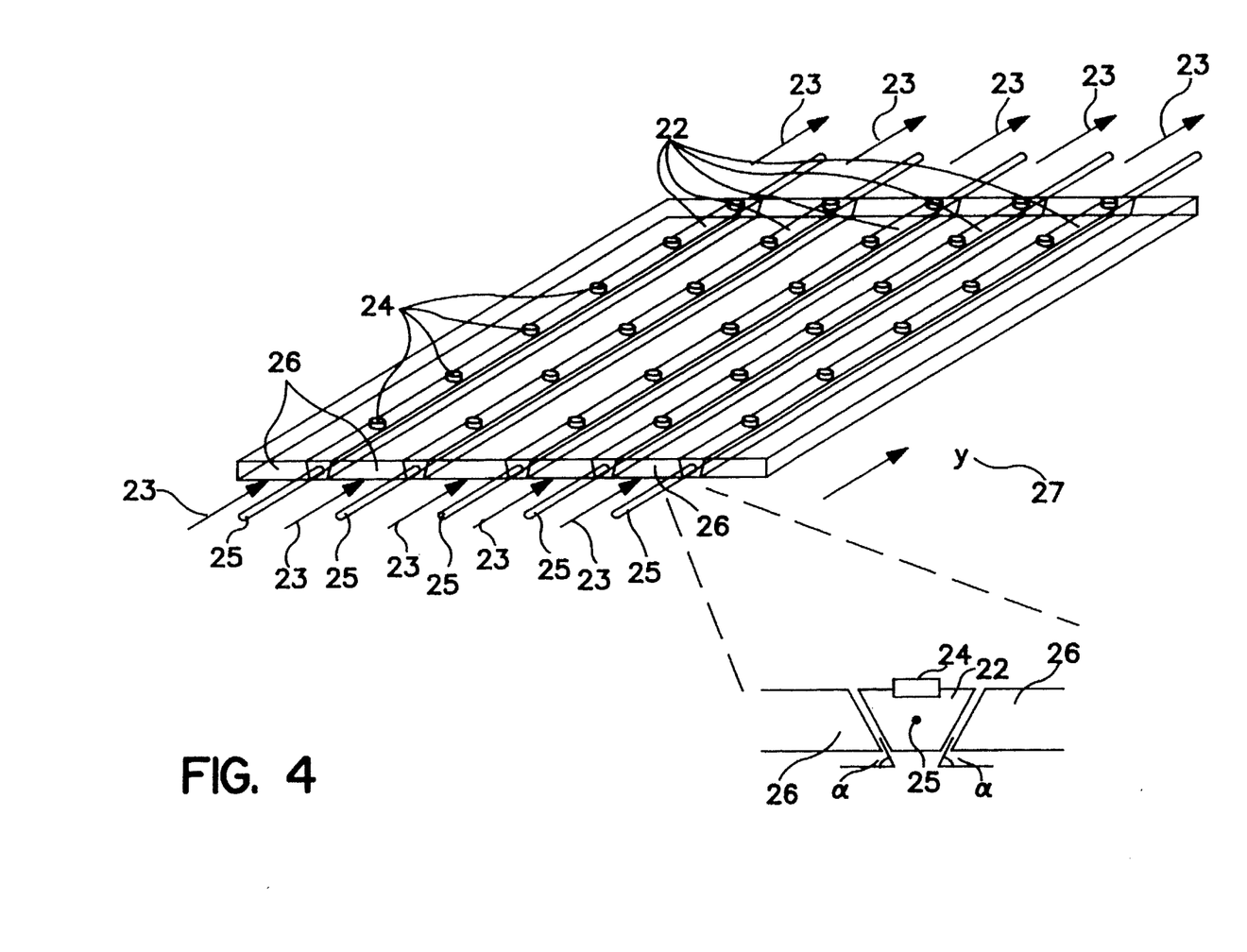
FIG. 4 is another example of a shield and an x-ray imaging system with which the method for scatter compensation according to the invention can be applied.

In FIG. 4 an example of a shield is given with which one embodiment of the method according to the invention can be realized. The shield will be positioned between the source and the object and the detector. A set of opaque lead disks 24 are distributed across the area of the shield. The disks 24 are fixed on long lucite strips 22 which are parallel. In the embodiment of FIG. 4 the distance along the strips 22 between the disks 24 is constant. These strips 22 can slide forward and backward in the direction of coordinate y 27. The strips 22 are positioned next to pieces of lucite 26 which have the same thickness as the lucite strips 22. The material of the strips 22 and of the pieces 26 does not have to be lucite, but in one embodiment we choose a material on which the disks 24 can be fixed and which does not strongly attenuate x-radiation. The pieces 26 are adjacent to the strips 22. In the embodiment of FIG. 4, at the positions where the strips 22 are adjacent to the pieces 26, the strips 22 and the pieces 26 have a small inclination angle $\alpha$. The reason for the angle $\alpha$ is that when x-radiation goes through the shield of FIG. 4, the angle $\alpha$ prohibits that in the x-ray image a narrow band, corresponding to the narrow air space between 22 and 26, of higher intensity appears next to the border positions of 22. In the embodiment of FIG. 4, the positions of the strips 22 is changed during a short interruption time of the exposure time T. During the short interruption time the strips 24 are moved 23 quickly in the direction of y over a distance which is half of the distance between two neighbouring disks 24 on a strip 22. The driving force 25 over the movement of strips 22 can be a magnetic force or any other force that can realize a quick movement in a short time. In one embodiment the fraction of the exposure time T before the interruption and after the interruption are the same and equal to 0.5. In this way the area under all of the disks is shielded by the disks during the half of the exposure time T. It is not necessary, but it is of course more simple.

Figure 5:
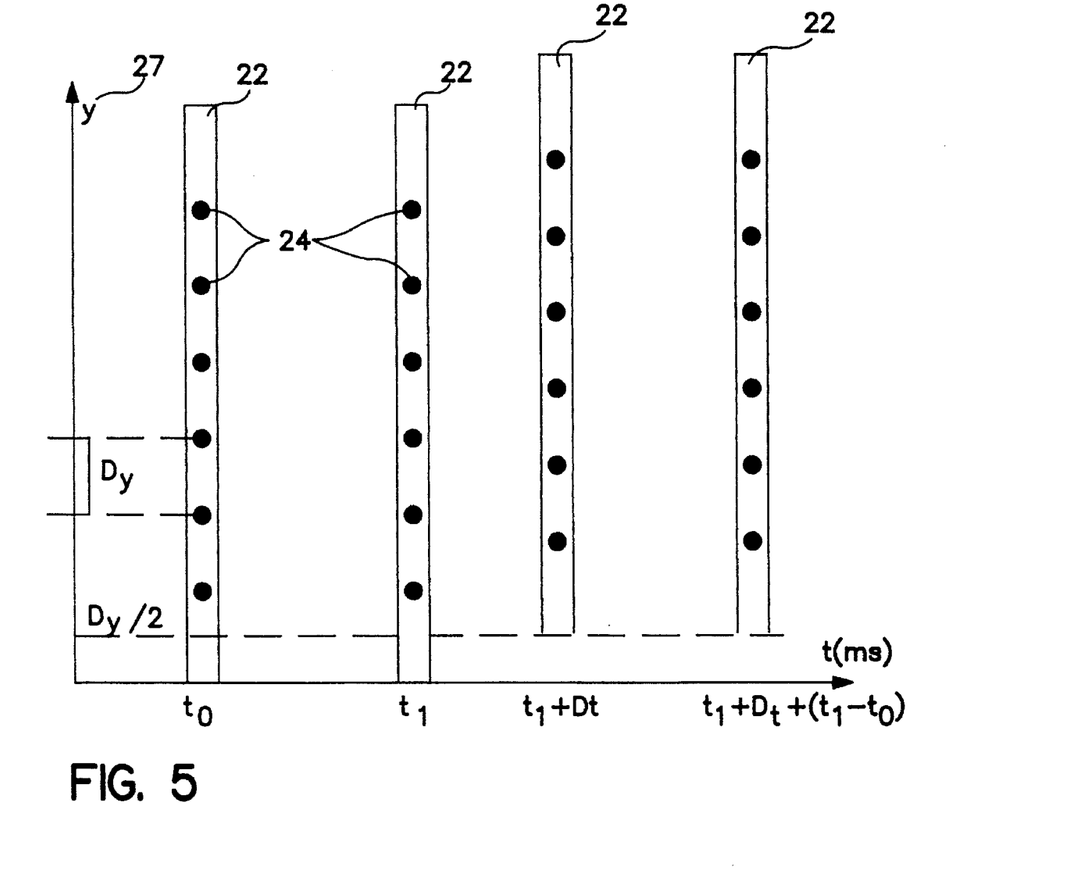
FIG. 5 is a schematic representation of the change in position of opaque shields in one embodiment of the method for compensation for scattered radiation according to the invention.

For the embodiment of FIG. 4, the position of strips 22 (and of its disk 24) in function of the time is shown in FIG. 5.

Referring to FIG. 5, the distance between the disks 24 along the strip 22 is Dy. Between time T0 and T1 the source is exposing the shield (and all the rest, i.e. object, detector). Thus, according to one embodiment (t1–t0)=T/2. At t1 the source is switched off for a short period of time DT. During this interruption of the exposure time the strip is moved along its length (in the direction of y 27) over a distance Dy/2. The distance does not have to be Dy/2, but in one embodiment it is chosen for realizing an equal distribution of shielded areas in the image. At time t1+Dt the source is again switched on for a period of time equal to T/2. The result is that all disks 24 shielded during T/2 areas of the object and of the detector. In this embodiment the spectrum of the x-radiation emitted by the x-ray source is not changed during the exposure time, though this is not essential. For reasons of simplicity the intensity is also taken constant, though it is not necessary. One could for example multiply the intensity of the x-radiation before the interruption time with a constant factor after the interruption time. It would be useless and it would just make everything more complicated. Therefor in a preferred embodiment we take a constant intensity.

Figure 6:
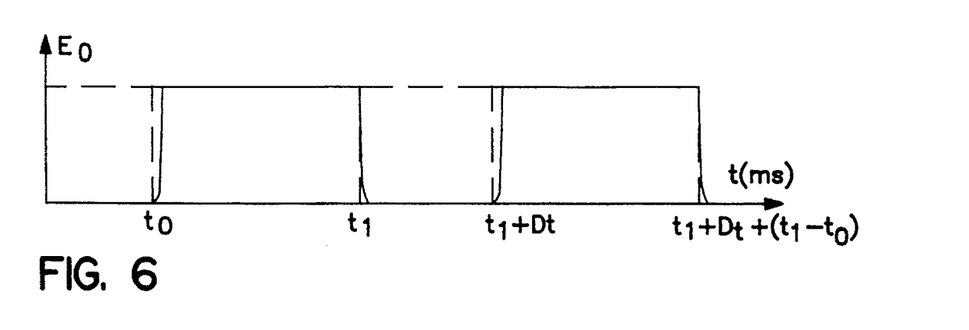
FIG. 6 is an example of how the intensity of the x-radiation emitted by an x-ray source and the exposure time can be applied for the embodiment of FIG. 5.

So for this embodiment, the intensity of the x-radiation emitted by the source during the exposure time and during the interruption time is shown in FIG. 6. Between time t0 and time t1 the source is switched on with an intensity E0 of the x-radiation. At t1 the source is switched off; thus the intensity is zero. At time t1+Dt the source is switched on again whereby the intensity of the x-radiation is again E0.

Figure 7:
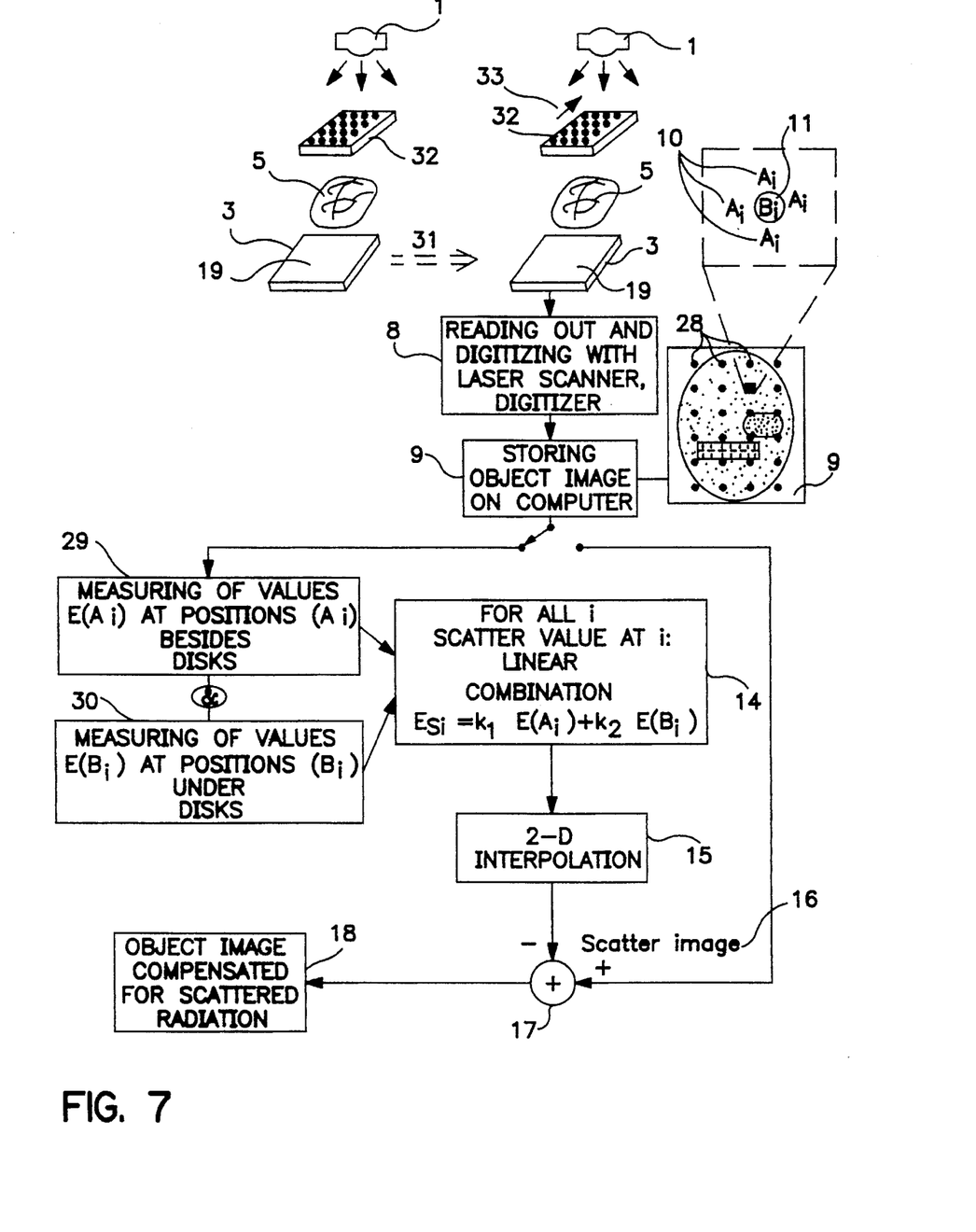
FIG. 7 is a functional block diagram illustrating another embodiment of the method for radiation scatter compensation according to the invention. The figure gives also an example of an x-ray imaging system with which the method for scatter compensation according to the invention can be applied.

The type of shield of the embodiment of FIG. 4 and the position of the opaque shields in time and space of the embodiments of FIG. 4, 5 and 6 is used in the embodiment of FIG. 7.

FIG. 7 is a schematic diagram of an embodiment of the method for compensating for scattered radiation according to the invention. The method will be realized on an x-ray imaging system, such as a computed radiographic system. This system is just an example. Other x-ray imaging systems are possible. X-Radiation from a source 1 is directed through an object 5 to an area detector such as a photostimulable phosphor screen 3 positioned in a visible light opaque cassette 19, whereby the x-ray image is latently stored on the phosphor screen 3. The latent image of phosphor screen 3 is then read out and digitized 8 by a laser scanner digitizer and converted into a grey value digitized image 8 which is stored on a computer and can be displayed. Radiation received by phosphor sheet 3 includes primary radiation but also a significant amount of scattered radiation which can cause a significant error in the displayed image. In accordance with the invention a calculation of the radiation scatter is determined and the image is then compensated by subtraction of the scattered radiation. After subtraction of the scattered radiation information about the primary radiation distribution is not lost in any location of the image. The calculation of the radiation scatter according to the invention is in the embodiment of FIG. 7 made possible by positioning a shield 32 between source 1 and object 5. One embodiment of a shield 32 is explained in FIG. 4. As explained in FIG. 5 and in FIG. 6, during the first half of exposure time T the source 1 is switched on and the shield 32 is exposed, then, the source is switched off for a short interruption time. During that interruption time the position of the opaque disks (24 in FIG. 4 and 5) on the shield is changed according to the embodiment of FIG. 4, 5 and 6.

This change of position is symbolized in FIG. 7 by 33. All disks have shielded during the half of the exposure time T the areas 28 underlying the disks before and after changing of their position. The disks shield the primary radiation. In the object image these areas 28 are clearly visible. Let us consider a set of locations i corresponding with the areas 28. We measure 13 the total detected intensity E(Bi) at position 11 Bi in an area 28 and we measure 12 the total detected intensities E(Ai) at positions 10 Ai next to position 11 Bi and next to the area 28. Since we assume basically that the radiation scatter has a low spatial frequency, we assume also that the amount of radiation scatter in position Bi and in positions Ai is the same. The mean primary radiation intensity nevertheless differs in position Bi and in positions Ai since Bi was shielded during fraction 0.5 of T. A fraction of the difference of the mean primary intensity signal in Bi and in Ai can be caused by the variations of tissues in the object in the surrounding of Bi and Ai. If these variations are not too large, we can interpolate the mean values of the primary intensities in the positions Ai around the area 28. At this stage we don't know yet the primary radiation distribution around the location i. The scattered radiation signal $E_{si}$ in the local surrounding of location i is more or less constant; thus interpolating the total signal in stead of only the primary radiation signal will not affect the scattered radiation signal. The further on, by E(Ai) is meant the mentioned interpolated value at position Bi. In this way the difference between the primary intensity signal in Bi and in Ai is only caused by the shielding Bi during fraction 0.5 of T. The radiation scatter intensity signal in position Bi is then given by 14:

$$E_{si}=k1.E(Ai)+k2.E(Bi)$$

whereby k1=−1 and k2=2. After having calculated 14 the radiation scatter $E_{si}$ for all locations i we interpolate 15 these radiation scatter values for the whole image area and we obtain the scatter image 16. The scatter image 16 is subtracted from the original image 9 to obtain the object image 18 compensated for scattered radiation. In image 18 the areas 28 are contrasting with the area next to them because the primary radiation intensity signal in the areas 28 is fraction 0.5 smaller then the primary radiation intensity signal just next to the areas. If wanted the image 18 can be compensated for the effect of the shielding in the area 28 by multiplying the primary intensity signal in an area 28 with factor 2. We can even more or less take into account the local profile of the radiation scatter in the areas 28 under the disks. Since under the opaque shields it self no first order radiation scatter (—this means radiation which scatters for the first time in the volume an opaque shield—) is generated, a small deviation from a constant radiation scatter value can appear. The error made by assuming that the radiation scatter is constant is a small error. Nevertheless, one can estimate the shape of the mentioned profile to be more accurate.

In the embodiment of FIG. 7 the exposure time T may be short. If human patients are involved it may be of the same order as for a conventional radiograph. Also the time of interruption can be very short.

The measuring of the signals may also be concurrent and does not have to be performed in a certain order.

The opaque shields in the embodiments of FIG. 4, 5, 6 and 7 do not have to be disks. They may have other shapes.

In the described embodiments the area detector is a photostimulable phosphor screen. Other area detectors such as a radiographic film may be envisioned. In case of a radiographic film radiation values are measured by scanning an exposed and processed film by means of light and detecting image-wise transmitted light.

I claim:

1. A method of compensating for scattered radiation in a 2-dimensional x-ray system comprising the steps of:

exposing an object and a radiation shield comprising a plurality of X-ray opaque bodies, to x-rays emitted by an x-ray source during an exposure time T, the shield being positioned between said x-ray source and said object, so that during a known fraction $f_j$ ($f_j$>0 and $f_j$<1) of said exposure time T a plurality of areas j of said object are temporarily shielded by said opaque bodies, exposing a two-dimensional radiation detector to x-rays transmitted by a combination of said object and said shield during said exposure time T, measuring radiation $E_1$ received by said detector at temporarily shielded areas j of said radiation detector, measuring radiation $E_2$ received by said detector in areas closely adjacent to said temporarily shielded areas j that have not been shielded by said opaque bodies during said exposure time T, calculating radiation scatter values $E_s$ received by said detector at said temporarily shielded areas j of said radiation detector, by using said fraction $f_j$ of said exposure time T and said measured radiation $E_1$ and said measured radiation $E_2$, calculating radiation scatter values for all areas of said detector means by interpolating the calculated radiation scatter values $E_s$, measuring radiation received by said radiation detector at all areas of said radiation detector where it has not yet been measured, and subtracting interpolated radiation scatter values from the measured radiation values for all areas of said radiation detector.

2. The method as defined by claim 1 wherein said exposure time is interrupted.

3. The method as defined in claim 2 wherein the position of said radiation shield is only changed during interruption of said exposure time.

4. The method as defined by claim 1 wherein measuring steps are concurrent.

5. A method according to claim 1 wherein said area detector is a photostimulable phosphor screen and wherein radiation is measured by scanning an exposed photostimulable phosphor screen with stimulating radiation, detecting light emitted upon stimulation and converting said light into an electric signal representation.

6. A method according to claim 1 wherein said area detector is a radiographic film and wherein radiation is measured by scanning an exposed and processed radiographic film with light and detecting light transmitted by said film.

* * * * *